(12) United States Patent
Shimotsu

(10) Patent No.: US 8,419,622 B2
(45) Date of Patent: Apr. 16, 2013

(54) OPTICAL FIBER CONNECTION STRUCTURE AND ENDOSCOPE SYSTEM

(75) Inventor: Shinichi Shimotsu, Kanagawa (JP)

(73) Assignee: Fujifilm Corporation (JP)

( * ) Notice: Subject to any disclaimer, the term of this patent is extended or adjusted under 35 U.S.C. 154(b) by 324 days.

(21) Appl. No.: 12/821,705

(22) Filed: Jun. 23, 2010

(65) Prior Publication Data

US 2010/0331626 A1    Dec. 30, 2010

(30) Foreign Application Priority Data

Jun. 25, 2009    (JP) .................. 2009-151202

(51) Int. Cl.
*A61B 1/07*    (2006.01)
*G02B 6/38*    (2006.01)

(52) U.S. Cl.
USPC ............. 600/132; 600/178; 600/182; 385/34; 385/74

(58) Field of Classification Search .............. 600/132, 600/178, 182; 385/34, 73, 74; 362/554, 362/572, 574

See application file for complete search history.

(56) References Cited

U.S. PATENT DOCUMENTS

| | | | | |
|---|---|---|---|---|
| 3,829,195 A | * | 8/1974 | Rawson | 385/34 |
| 4,360,249 A | * | 11/1982 | Slemon | 385/51 |
| 4,712,862 A | * | 12/1987 | Lightstone | 385/73 |
| 4,718,746 A | * | 1/1988 | Chrepta | 385/74 |
| 4,818,049 A | * | 4/1989 | Assenheim et al. | 385/35 |
| 5,039,193 A | | 8/1991 | Snow et al. | |
| 5,359,683 A | | 10/1994 | Pan | |
| 5,423,312 A | * | 6/1995 | Siegmund et al. | 600/109 |
| 5,659,644 A | * | 8/1997 | DiGiovanni et al. | 385/31 |
| 5,872,879 A | * | 2/1999 | Hamm | 385/25 |
| 6,035,084 A | * | 3/2000 | Haake et al. | 385/49 |
| 6,110,107 A | * | 8/2000 | Bellahsene et al. | 600/182 |
| 6,302,593 B1 | | 10/2001 | Haake | |
| 6,542,665 B2 | | 4/2003 | Reed et al. | |

(Continued)

FOREIGN PATENT DOCUMENTS

| | | |
|---|---|---|
| EP | 1 168 012 A2 | 1/2002 |
| EP | 1 298 459 A2 | 4/2003 |
| JP | 2006-154868 A | 6/2006 |
| WO | 03/010564 A2 | 2/2003 |

OTHER PUBLICATIONS

The Extended European Search Report dated Sep. 7, 2010; Application No. 10167164.2-1524.

(Continued)

*Primary Examiner* — John P Leubecker
(74) *Attorney, Agent, or Firm* — Studebaker & Brackett PC; Donald R. Studebaker

(57) ABSTRACT

A first fiber stub incorporating a first GI fiber is connected to a first optical fiber by a PC connection. The first GI fiber expands a beam diameter of light transmitted by the first optical fiber and collimates this light. A second fiber stub is connected to a second optical fiber by the PC connection. The second fiber stub, facing the first fiber stub across a predetermined gap G therebetween, converges the light transmitted from the first fiber stub using a second GI fiber incorporated therein. The second fiber stub transmits the converged light to the second optical fiber. When the first fiber stub or the second fiber stub is damaged, the first fiber stub or the second fiber stub is pulled out from a first sleeve or a second sleeve, respectively for replacement.

14 Claims, 4 Drawing Sheets

U.S. PATENT DOCUMENTS

| | | |
|---|---|---|
| 6,546,169 B1 | 4/2003 | Lin et al. |
| 6,854,900 B2 * | 2/2005 | Lai et al. .................. 385/80 |
| 7,333,702 B2 | 2/2008 | Fujita et al. |
| 7,334,944 B1 * | 2/2008 | Uhlhorn et al. ............ 385/74 |
| 7,758,255 B2 * | 7/2010 | Jones ........................ 385/73 |
| 7,885,500 B2 * | 2/2011 | Popp et al. ................ 385/52 |
| 8,182,159 B2 * | 5/2012 | Tanaka ...................... 385/74 |
| 2002/0076148 A1 * | 6/2002 | DeRosa et al. ............ 385/27 |
| 2002/0085797 A1 | 7/2002 | Freakes |
| 2002/0114606 A1 * | 8/2002 | De Bougrenet et al. ... 385/140 |
| 2002/0146202 A1 | 10/2002 | Reed et al. |
| 2003/0206696 A1 * | 11/2003 | Gerber et al. ............. 385/33 |
| 2004/0175073 A1 * | 9/2004 | Grinderslev et al. ...... 385/34 |
| 2008/0087323 A1 * | 4/2008 | Araki et al. ............... 136/256 |
| 2010/0027943 A1 * | 2/2010 | Armani et al. ............ 385/74 |
| 2010/0104244 A1 * | 4/2010 | Grinderslev ............... 385/74 |

OTHER PUBLICATIONS

The European Office Action "The Communication pursuant to Article 94(3) EPC" dated Nov. 6, 2012 which corresponds to EP Application No. 10 167 164.2-1524 and is related to U.S. Appl. No. 12/821,705.

* cited by examiner

FIG. 2

| | CONNECTION LOSS (405 nm) | CONNECTION LOSS (635 nm) |
|---|---|---|
| SAMPLE A<br>FIRST GI FIBER LENGTH: 4.62 mm<br>SECOND GI FIBER LENGTH: 3.91 mm | 1.2dB<br>(LOSS 24%) | 0.9dB<br>(LOSS 18%) |
| SAMPLE B<br>FIRST GI FIBER LENGTH: 4.62 mm<br>SECOND GI FIBER LENGTH: 3.93 mm | 1.4dB<br>(LOSS 28%) | 1.2dB<br>(LOSS 22%) |

OPTICAL FIBER CONNECTION STRUCTURE AND ENDOSCOPE SYSTEM

BACKGROUND OF THE INVENTION

1. Field of the Invention

The present invention relates to a detachable connection structure for connecting optical fibers and an endoscope system using this connection structure, and more particularly relates to a connection structure of optical fibers suitable for transmitting short-wavelength, high-power laser light and the endoscope system using this connection structure.

2. Description of the Related Art

A physical contact connection (hereinafter referred to as the PC connection) is a generally used method for connecting optical fibers, in which ends of the optical fibers are tightly made into contact with each other. Each optical fiber used in the PC connection is inserted through and fixed in a cylindrical ferrule, and an end surface of the optical fiber is polished into a convex spherical surface together with an end surface of the ferrule. The ferrules with the optical fibers are inserted into opposite ends of a cylindrical sleeve, and the end surfaces of the ferrules are made into contact with each other inside the sleeve. Owing to this, the optical fibers exposed from the end surfaces of the ferrules are directly and tightly made into contact with each other.

Endoscopes are widely used for examining the inside of human bodies. The endoscope has an insertion section which is inserted into the body, and an operation section for controlling directions of a tip of the insertion section. Through the insertion section, a light guide for sending illumination light is inserted. This light guide is a fiber bundle which is composed of a plurality of optical fibers tied together. An end of the light guide is connected to a lighting window provided at a distal end of the insertion section. The other end of the light guide is connected to a light source unit via a connector using the PC connection.

Since the connector of the endoscope is frequently attached and detached, dust or the like tend to be adhered to the end of the optical fiber. In addition, the end of the optical fiber may be damaged and has flaws due to the impact of the attachment or detachment of the connector. If the end of the optical fiber gets dusty or flawed, a connection loss increases. In addition, if the optical fiber end has high optical power density, the dust adhered or the flaws thereon may catch fire, and the end of the optical fiber and the end of the ferrule may be burnt. Otherwise, the fire may spread over the optical fiber by a fiber fuse phenomenon.

In order to prevent the burn of the optical fiber due to the adhered dust or the like, there is known an optical fiber transmission path in which the optical power density is lowered at the connection part of the optical fibers. According to U.S. Pat. Nos. 7,333,702 (corresponding to Japanese Patent Laid-Open Publication No. 2005-077549) and 6,542,665 (corresponding to Japanese Patent Laid-Open Publication No. 2002-350666), for example, a graded-index fiber that functions as a collimator lens is connected to an end of a single-mode fiber by fusion splicing, so that a mode field diameter is expanded.

By the way, it is considered to use a laser light source unit as a light source of the endoscope. In the laser light source unit, laser light with short wavelength and high power is guided through the light guide to a phosphor disposed near the lighting window, and the phosphor is excited by the laser light to emanate illumination light. In the light guide used in the laser light source unit, a single strand of multi-mode fiber having a large core diameter of, for example, at least 100 μm is used instead of the optical fiber bundle. Owing to the use of the laser light source for the endoscope, a diameter of the insertion section of the endoscope can be reduced.

It is known that when the optical fiber transmits short-wavelength, high-power laser light, a phenomenon called dust collection effect occurs at a light transmission part where the optical power density is high. The dust collection effect is a phenomenon in which the laser light photochemically reacts with vaporized organic substances and forms other substances, and the formed substances are deposited. Since the multi-mode fiber has a lager core diameter than a general single-mode fiber, it is difficult to precisely contact the end surfaces of the cores of the multi-mode fibers with each other by the PC connection. As a result, apart of the end surface of the core with high optical power density is exposed to air, which causes the dust collection effect. The occurrence of the dust collection effect in the optical fiber increases the connection loss, like the case where dust adheres to the end of the optical fiber, and may causes the burn of the optical fiber or the fiber fuse phenomenon.

When the connected optical fibers transmit the short-wavelength, high-power laser light, there is a case where oxide (such as quartz and $SIO_2$) contained in the optical fibers reacts with the laser light, and the ends of the optical fibers adhere to each other in the PC connection section. It is known that this adhesion phenomenon is likely to occur when the ends of the optical fibers or the ends of the ferrules are connected by the PC connection after UV cleaning. If the optical fibers adhere to each other in the connector of the endoscope, the ends of the optical fibers will break upon detaching the connector from the laser light source unit. If the ends of the optical fibers are broken, they need to be re-polished with the ferrules, which is a big repair.

Such dust collection effect and adhesion phenomenon can be prevented by lowering the optical power density at the PC connection section with use of the graded-index fibers like the devices disclosed in the U.S. Pat. Nos. 7,333,702 and 6,542,665. However, since these devices use the single-mode fibers and assume to transmit long-wavelength light for communications, the type and the core diameter of the optical fibers being used are different from those of the laser light source unit, and it is difficult to simply replace the light with the laser light.

SUMMARY OF THE INVENTION

It is an object of the present invention to prevent dust collection effect, adhesion phenomenon and the like which occur when an optical fiber transmits short-wavelength, high-power laser light, while facilitating repair of an optical fiber connection structure being damaged.

In order to achieve the above and other objects, an optical fiber connection structure according to the present invention has a first graded-index fiber and a second graded-index fiber. The first graded-index fiber has a core diameter at least three times larger than that of a first optical fiber and is detachably attached to one end of the first optical fiber. The first graded-index fiber expands a beam diameter of light from the first optical fiber and collimates this light. The second graded-index fiber has a core diameter equal to or larger than that of the first graded-index fiber and is detachably attached to one end of the second optical fiber. The first graded-index fiber and the second graded-index fiber are spaced apart from each other with a predetermined gap. The second graded-index fiber converges the beam diameter of the light from the first graded-index fiber and causes the light enter the second optical fiber. The first and second optical fibers are multi-mode fibers each of which has a core diameter of at least 100 µm. The light with an optical power of at least 100 mW is transmitted from the first optical fiber to the second optical fiber.

The first and second optical fibers transmit one or more beams of light with different wavelengths of 405 nm to 635 nm. The diameters of the first graded-index fiber and the second graded-index fiber are preferably at least five times larger than that of the first optical fiber. The length of the first graded-index fiber is preferably longer than the length of the second graded-index fiber. A total length of the first and second graded-index fibers is preferably ½λ or an integral multiple of ½λ. The lengths of the first graded-index fiber and the second graded-index fiber are preferably at least 3 mm and at most 10 mm.

A light exit surface of the first graded-index fiber from which the light is output and a light incident surface of the second graded-index fiber to which the light is entered may be provided with an anti-reflection layer having fluoride at its outermost surface.

A light incident surface of the first graded-index fiber and a light exit surface of the second graded-index fiber may be provided with a fluoride layer.

The optical fiber connection structure of the present invention has a first connection member, a first optical component, a first holding member, a second connection member, a second optical component, a second holding member, and a joining member. The first connection member is attached to the end of the first optical fiber such that the end of the first optical fiber is exposed from one end surface of the first connection member. The first optical component houses the first graded-index fiber such that the light incident surface and the light exit surface of the first graded-index fiber are exposed from both ends of the first optical component. The first holding member holds the first connection member and the first optical component such that the end of the first optical fiber and the light incident surface of the first graded-index fiber are in contact with each other. The second connection member is attached to the end of the second optical fiber such that the end of the second optical fiber is exposed from one end surface of the second connection member. The second optical component houses the second graded-index fiber such that the light incident surface and the light exit surface of the second graded-index fiber are exposed from both ends of the second optical component. The second holding member holds the second connection member and the second optical component such that the end of the second optical fiber and the light exit surface of the second graded-index fiber are in contact with each other. The joining member joins the first optical component and the second optical component such that the light exit surface of the first graded-index fiber and the light incident surface of the second graded-index fiber are faced across with a predetermined gap.

Preferably, the first and second connection members are first and second ferrules, and the first and second holding members are first and second sleeves, and the first and second optical components are first and second fiber stubs, and the joining member is a connection sleeve.

An endoscope system according to the present invention includes an endoscope, a light source unit and an optical fiber connection structure. The endoscope captures images while illuminating inside a human body using an optical fiber inserted through an insertion section of the endoscope. The light source unit has a light source which generates light with an optical power of at least 100 mW. The light source unit sends the light to the optical fiber. The optical fiber connection structure has the first connection member, the first optical component, the first holding member, the second connection member, the second optical component, the second holding member and the joining member, and connects the optical fiber of the endoscope and the light source of the light source unit.

According to the present invention, burn and spread of fire of the optical fiber due to the adhered dust or the like, and flaws of the end of the optical fiber can be prevented. In addition, the dust collection at the end of the optical fiber and the adhesion phenomenon of the optical fibers at the PC connection part can be prevented. Moreover, even if the optical fiber gets dirty due to the dust collection effect and the like, the optical fiber connection structure according to the present invention can be repaired with ease by simply replacing the graded-index fibers.

BRIEF DESCRIPTION OF THE DRAWINGS

Fore more complete understanding of the present invention, and the advantage thereof, reference is now made to the following descriptions taken in conjunction with the accompanying drawings, in which:

FIG. 2 is a table showing evaluation results of connection loss;

DESCRIPTION OF THE PREFERRED EMBODIMENTS

Figure 1:
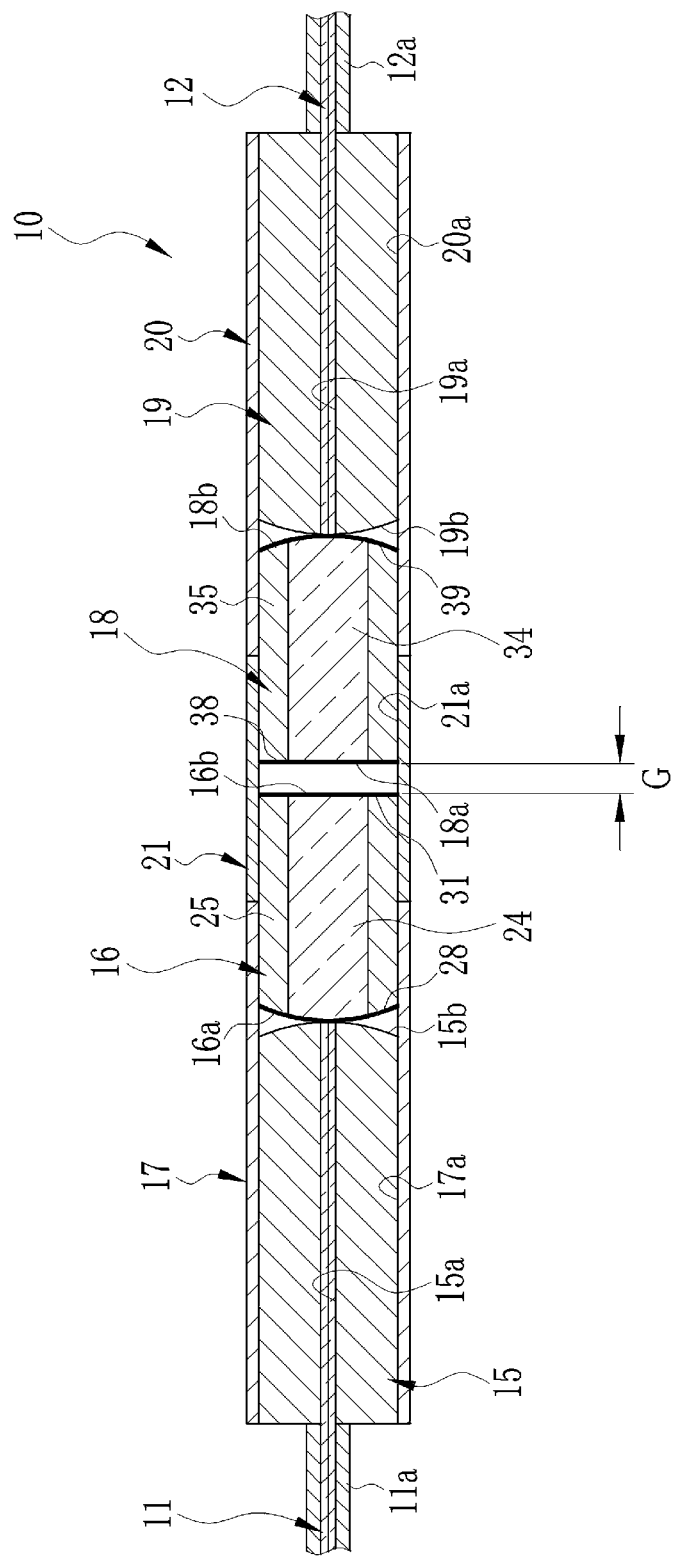
FIG. 1 is a longitudinal sectional view of a connection structure of optical fibers according to the present invention.

In FIG. 1, a first optical fiber 11 and a second optical fiber 12 are connected using an optical fiber connection structure 10 of the present invention. In this embodiment, laser light having a short wavelength of, for example, 405 nm to 635 nm and a high power of, for example, at least 100 mW is transmitted from the first optical fiber 11 toward the second optical fiber 12. The first optical fiber 11 and the second optical fiber 12 are quartz multi-mode fibers having a core diameter of, for example, at least 100 µm.

The connection structure 10 includes a first ferrule 15 for holding an end of the first optical fiber 11, and a first fiber stub 16 which expands a beam diameter of the laser light transmitted by the first optical fiber 11 and collimates this laser light. The first ferrule 15 and the first fiber stub 16 are detachably connected using a first sleeve 17. The connection structure 10 also includes a second fiber stub 18 which converges the light transmitted from the first optical fiber 11 via the first fiber stub 16, and a second ferrule 19 for holding an end of the second optical fiber 12. The second fiber stub 18 and the second ferrule 19 are detachably connected using a second sleeve 20. The first fiber stub 16 and the second fiber stub 18 are detachably connected using a connection sleeve 21. When either one or both of the first fiber stub 16 and the second fiber stub 18 are pulled out of the connection sleeve 21, the connection is released.

The first ferrule 15 has a cylindrical shape through which a fiber insertion hole 15a is provided at the center thereof in an axial direction. The optical fiber 11 whose jacket 11a is stripped at the tip is inserted through the fiber insertion hole 15a and fixed therein using an adhesive material. Although the drawing in FIG. 1 is simplified in order to show a summary of the present invention, the first optical fiber 11 and the first ferrule 15 are actually connected such that a metal flange fixed to a base side of the first ferrule 15 holds the first optical fiber 11. A tip 15b of the first ferrule 15 and the tip of the first optical fiber 11 inserted through the first ferrule 15 are ground together into a convex spherical surface or a plane surface.

The first fiber stub 16 includes a first graded-index fiber (hereinafter, referred to as the GI fiber) 24 used as a collimator lens, and a cylindrical ferrule 25 incorporating the first GI fiber 24 therein. An Incident surface 16a of the first ferrule 16 exposing one tip of the first GI fiber 24 is ground into a convex spherical surface and an exit surface 16b of the first ferrule 16 exposing the other tip of the first GI fiber 24 is ground into a plane surface. The incident surface 16a is made into close contact with the tip 15b of the first ferrule 15, and thereby the first GI fiber 24 is connected to the first optical fiber 11 in the PC connection. Note that a combination of shapes of the incident surface 16a and the exit surface 16b (the shape of the incident surface 16a/the shape of the exit surface 16b) may be spherical/spherical, plane/spherical, spherical/plane or plane/plane.

Since the first GI fiber 24 has a core diameter larger than the first optical fiber 11, the first optical fiber 11 can be connected, by the PC connection, to the first GI fiber 24 without exposing its tip to air. Owing to this, dust collection effect is not induced at the tip of the first optical fiber 11. A mechanism for pressing one of the first ferrule 15 and the first fiber stub 16 against the other is provided so that the PC connection between the first optical fiber 11 and the first GI fiber 24 are maintained in a favorable condition. When the core diameters of the optical fibers are at least 100 µm, preferable shape combinations of the contact surfaces are spherical/plane and plane/plane as compared to spherical/spherical in view of prevention of contamination since the former two combinations have larger contact surfaces.

Since the first GI fiber 24 expands the beam diameter of the laser light transmitted by the first optical fiber 11 and collimates this laser light, optical power density at the exit surface 16b of the first fiber stub 16 becomes lower than that at the tip of the first optical fiber 11. Owing to this, optical loss due to dust and scratches on the exit surface 16b is prevented. In addition, damages of the first fiber stub 16 due to burning of the dust and the like and damages of the first optical fiber 11 due to the fiber fuse phenomenon are also prevented. Further, since photochemical reaction between the laser light and organic substances in the air is lowered due to decrease of the optical power density, occurrence of the dust collection effect on the exit surface 16b is also lowered.

It is known that the dust collection effect can be sufficiently prevented by controlling the optical power density to at most 15 W/mm$^2$ (see for example, Japanese Patent Laid-Open Publication No. 2007-025431). Therefore, it is preferable that the optical power density at the exit surface 16b is lowered to at most 15 W/mm$^2$ in this embodiment.

The incident surface 16a of the first fiber stub 16 is provided with a fluoride layer 28. For this configuration, the first optical fiber 11 is connected to the first GI fiber 24, by the PC connection, through the fluoride layer 28, and therefore preventing an adhesion phenomenon in which the contact surfaces of the optical fibers connected by the PC connection are adhered.

The exit surface 16b of the first fiber stub 16 is provided with an anti-reflection layer 31 for decreasing reflection loss. An outermost layer of the anti-reflection layer 31 is provided with a layer of fluoride. Therefore, the dust adhered to or accumulated due to the dust collection effect can be removed with ease.

The first sleeve 17, generally called a split sleeve, has a cylindrical shape and is provided with a ferrule insertion hole 17a at the center thereof. An inner diameter of the insertion hole 17a is slightly smaller than external diameters of the first ferrule 15 and the first fiber stub 16. The first sleeve 17 has a slit (not shown) on its peripheral surface along its axis which gives elasticity to the first sleeve 17 in a radial direction.

The first ferrule 15 and the first fiber stub 16 are inserted into the ferrule insertion hole 17a from opposite ends of the first sleeve 17, and detachably held owing to the elasticity of the first sleeve 17. The tip 15b of the first ferrule 15 and the incident surface 16a of the first fiber stub 16 are made into close contact with each other inside the first sleeve 17.

Since the length of the first sleeve 17 is shorter than the total length of the first ferrule 15 and the first fiber stub 16, approximately half the length of the first fiber stub 16 is exposed from one end of the first sleeve 17 when a rear end of the first ferrule 15 is aligned with the other end of the first sleeve 17. Note that the first sleeve 17 may be made of various materials such as metal and zirconia ceramics.

The second fiber stub 18 is about the same as the first fiber stub 16 and includes a second GI fiber 34 and a cylindrical ferrule 35 incorporating the second GI fiber 34 therein. An incident surface 18a of the second ferrule 18 exposing one tip of the second GI fiber 34 is ground into a plane surface and an exit surface 18b of the second ferrule 18 exposing the other tip of the second GI fiber 34 is ground into a convex spherical surface.

The incident surface 18a of the second fiber stub 18 is faced to the exit surface 16b of the first ferrule 16 at a predetermined gap G therebetween. The exit surface 18b of the second fiber stub 18 is made into close contact with a tip of the second ferrule 19, and thereby the second optical fiber 12 is connected to the second GI fiber 34 by the PC connection. Like the first fiber stub 16, the incident surface 18a and the exit surface 18b are provided with an anti-reflection layer 38 and a fluoride layer 39, respectively.

Since the first fiber stub 16 and the second fiber stub 18 are not made into contact at the exit surface 16b and the incident surface 18a, dust adhered to one of the exit surface 16b and the incident surface 18a will not be crushed and spread. Since the first fiber stub 16 and the second fiber stub 18 do not come into contact with each other when the first optical fiber 11 and the second optical fiber 12 are connected or disconnected, flaws or damages do not occur.

The second ferrule 19 is about the same as the first ferrule 15 and holds a tip of the second optical fiber 12 like the first ferrule 15. A tip 19b of the second ferrule 19 and the tip of the second optical fiber 12 are ground together into a convex spherical surface or a plane surface.

The second sleeve 20 is about the same as the first sleeve 17 and detachably connecting the second fiber stub 18 and the second ferrule 19. The second optical fiber 12 and the second GI fiber 34 are connected by the PC connection inside the second sleeve 20. Approximately half the length of the second fiber stub 18 is held by the second sleeve 20 and the remaining is exposed from one end of the second sleeve 20. The connection sleeve 21 has a cylindrical shape through which a stub insertion hole 21a is provided at the center thereof. An inner diameter of the stub insertion hole 21a is approximately same as external diameters of the first fiber stub 16 and the second fiber stub 18. The first fiber stub 16 and the second fiber stub 18 are fitted into opposite ends of the stub insertion hole 21a of the connection sleeve 21, and thereby detachably connected with their center axes aligned. Note that the connection sleeve 21 may be made of various materials such as metal and zirconia ceramics.

The length of the connection sleeve 21 is equal to the total of the length which the first fiber stub 16 is exposed from the first sleeve 17, the length which the second fiber stub 18 is exposed from the second sleeve 20, and the gap G between the first fiber stub 16 and the second fiber stub 18. When the first fiber stub 16 and the second fiber stub 18 are fitted into the connection sleeve 21, the opposite ends of the connection sleeve 21 are in close contact to the first sleeve 17 and the second sleeve 20, which restricts lengths or amounts of the first fiber stub 16 and the second fiber stub 18 to be inserted into the connection sleeve 21. Owing to this, the predetermined gap G can be formed between the first fiber stub 16 and the second fiber stub 18 inside the connection sleeve 21.

It is found that a maximum dimension of the dust adhered to the tip of the optical fibers is approximately 50 μm. In view of this, the gap G between the exit surface 16b of the first fiber stub 16 and the incident surface 18a of the second fiber stub 18 is required to be at least 50 μm to prevent that the adhered dust is caught and crushed therebetween. Moreover, it is necessary to make sure that the first fiber stub 16 and the second fiber stub 18 are not in contact with each other. Therefore, the gap G is preferably about 0.5 mm to 2.0 mm in view of production error or assembly error of respective components of the connection structure 10.

Hereinafter, the first GI fiber 24 and the second GI fiber 34 are explained in detail. As mentioned above, the first optical fiber 11 and the second optical fiber 12 are multi-mode fibers whose core diameters are larger than that of a single-mode fiber generally used for communication. To increase the beam diameter of the laser light transmitted by the first optical fiber 11 and collimate this laser light while the dust collection effect or damages are prevented, a core diameter of the first GI fiber 24 needs to be at least three times, and more preferably at least five times larger than the core diameter of the first optical fiber 11.

Likewise, to appropriately converge the beam diameter of the laser light, which has been expanded by the first GI fiber 24, and transmit this laser light to the second optical fiber 12, a core diameter of the second GI fiber 34 needs to be at least equal to, or larger than the core diameter of the first GI fiber 24. In this embodiment, the core diameter of the first GI fiber 24 is, for example, at least 200 μm, and preferably at least 500 μm, and the core diameter of the second GI fiber 34 is equal to or larger than the diameter of the first GI fiber 24.

Since the GI fiber has large transmission loss for short-wavelength light, the lengths of the first GI fiber 24 and the second GI fiber 34 are preferably as short as possible. Moreover, since the end surfaces of the first GI fiber 24 and the second GI fiber 34 are ground after being inserted into the ferrules 25 and 35, respectively, the first GI fiber 24 and the second GI fiber 34 need to have enough lengths to be held while being ground. In view of the above, the lengths of the first GI fiber 24 and the second GI fiber 34 are, for example, at least 3 mm and at most 10 mm in this embodiment.

The mode field diameter (MFD) of the light transmitted through the GI fiber continuously changes with the following pattern: from minimum value to maximum value to minimum value to maximum value as one period (one pitch). Therefore, when the GI fiber is used as the collimator lens, the length thereof should be ¼ pitch. That is, the lengths of the first GI fiber 24 and the second GI fiber 34 are preferably ¼ pitch, while they are at least 3 mm and at most 10 mm as mentioned above. Although an optimal pitch is generally calculated by the following equation: ¼×(2n−1), (n=0, 1, 2, . . . ), ¼ pitch which is the minimum value is the preferable length in view of low transmission loss.

Hereinafter, an operation of the above-described embodiment is explained. The tip of the first optical fiber 11 is detachably connected to the first fiber stub 16 in the PC connection by the first ferrule 15 and the first sleeve 17. Like the first optical fiber 11, the tip of the second optical fiber 12 is detachably connected to the second fiber stub 18 in the PC connection by the second ferrule 19 and the second sleeve 20.

When the first optical fiber 11 and the second optical fiber 12 are connected, the first fiber stub 16 and the second fiber stub 18 are fitted into the opposite ends of the connection sleeve 21. The predetermined gap G is formed between the first fiber stub 16 and the second fiber stub 18 inside the connection sleeve 21 when the opposite ends of the connection sleeve 21 are contacted to the first sleeve 17 and the second sleeve 20, respectively. For this configuration, it is prevented that dust adhered to one of the first fiber stub 16 and the second fiber stub 18 is crushed and spread, or the first stub 16 and the second fiber stub 18 are damaged by inappropriately contacting with each other.

The other tip of the first optical fiber 11 opposite to the tip fixed to the first ferrule 15 is connected to a laser module, which generates laser light having a short wavelength of, for example, 405 nm to 635 nm and a high power of, for example, at least 100 mW. The laser light transmitted by the first optical fiber 11 is output from the tip of the first optical fiber 11 and then enters the first GI fiber 24 of the first fiber stub 16. The first GI fiber 24 expands the beam diameter of the laser light and collimates this laser light. The laser light is then output from the exit surface 16b. The second fiber stub 18 converges the beam diameter of the laser light entered from the first fiber stub 16 via the predetermined gap G and then sends the laser light to the second optical fiber 12.

It is hard to suppress the reflection perfectly even with use of the anti-reflection layers, and this may be a part of light source fluctuations. In addition, the connection loss sharply increases when the length of the first fiber stub 16 becomes shorter than ¹⁄₄₂λ pitch. To control these, it is preferable that the length of the first fiber stub 16 is longer than the length of the second fiber stub 18, so that the first GI fiber 24 and the second GI fiber 34 are asymmetry. In this case, a total length of the first and second GI fibers 24 and 34 is preferably ½λ or an integral multiple of ½λ.

The first optical fiber 11 and the second optical fiber 12 are connected, by the PC connection, to the first GI fiber 24 and the second GI fiber 34, respectively. Since he first GI fiber 24 and the second GI fiber 34 have larger core diameters as compared to the first optical fiber 11 and the second optical fiber 12, respectively, the first optical fiber 11 and the second optical fiber 12 are prevented from being exposed to air. Owing to this, dust collection effect is not induced. In addition, since the incident surface 16a of the first fiber stub 16 is provided with the fluoride layer 28, the adhesion phenomenon is not induced between the first optical fiber 11 and the first GI fiber 24. Likewise, the adhesion phenomenon is not induced between the second optical fiber 12 and the second GI fiber 34 owing to the fluoride layer 39 provided to the exit surface 18b.

Sometimes, dust and the like may be adhered to the exit surface 16b of the first fiber stub 16 or the incident surface 18a of the second fiber stub 18 when they are connected or disconnected. Since the optical power density of the laser light output from the exit surface 16b is lowered by the first GI fiber 24, the connection loss is not substantially increased. In addition, the adhered dust and the like may not be burned which may cause damages on the first fiber stub 16 and the second fiber stub 18. Moreover, the occurrence of dust collection effect is also decreased. Since the exit surface 16b and the incident surface 18a are respectively provided with the antireflection layers 31 and 38 which have the fluoride layer as its outermost layer, the adhered or accumulated dust can be removed with ease.

When the connection between the first optical fiber 11 and the second optical fiber 12 is released, one or both of the first fiber stub 16 and the second fiber stub 18 are pulled out of the connection sleeve 21. Since the first fiber stub 16 and the second fiber stub 18 are disposed with the gap G therebetween, the first fiber stub 16 and the second fiber stub 18 are not damaged due to the adhesion phenomenon when they are disconnected.

If the first fiber stub 16 is damaged, or deteriorated due to the accumulation of dust and the like, the first fiber stub 16 being used is pulled out of the first sleeve 17 and can be replaced with a new one. Although the conventional connection structure of optical fibers needed a repair by grinding the ferrule again, the present invention facilitates the repair of the connection structure, which results in cost reduction. The second fiber stub 18 can be replaced in the same manner as the first fiber stub 16.

Since the optical axes (centers) of the first fiber stub 16 and the second fiber stub 18 coincide with the optical axes of the first optical fiber 11 and the second optical fiber 12, the influence of chromatic aberration hardly appears. Therefore, the transmission loss of the laser lights having wavelengths in the range of 405 nm (blue-violet) to 635 nm (red) can be extremely small. Accordingly, the connection structure of the present invention is applicable to a system using laser lights of various wavelengths.

EXAMPLES

A connection loss caused by the connection structure 10 according to the present invention was evaluated. In the evaluation, a connection loss in a state in which the first optical fiber 11 and the second optical fiber 12 are directly connected was used as a reference, and increase in the connection loss caused by disposing the first fiber stub 16 and the second fiber stub 18, which are the targets of the evaluation, between the first optical fiber 11 and the second optical fiber 12 was compared to the reference and evaluated as the connection loss. In addition, the positions of the first fiber stub 16 and the second fiber stub 18 were adjusted according to the wavelength of 405 nm on a stage, and the connection loss of the laser light having the wavelength of 405 nm and that of the laser light having the wavelength of 635 nm were evaluated at the same positions. Since the laser light having the wavelength of 405 nm approximates 400 μm the optical axis direction due to wavelength dispersion as compared to the laser light having the wavelength of 635 nm, the positions of the fiber stubs 16 and 18 need to be adjusted to an optimal position according to the laser light of 405 nm. Conditions on the loss evaluation are as follows.

[First Optical Fiber and Second Optical Fiber]
 Multi-mode fibers (step index type)
 Core diameter: 105 μm
 Clad diameter: 125 μm
[First Ferrule and Second Ferrule]
 Zirconia ferrules having a diameter φ of 2.5 mm and a length of 10 mm
[First Fiber Stub and Second Fiber Stub]
 First GI fiber and second GI fiber
  Graded-index fibers (Ge doped core)
  Core diameter: 500 μm
  Clad diameter: 625 μm
  Length: 4.0 mm
  NA: 0.22
  Length of one pitch: approximately 8 mm Ferrule
  Zirconia ferrule having a diameter φ of 2.5 mm and a length of 4 mm
 Adhesive material
  Thermosetting epoxy
 Gap G
  1.0 mm to 1.5 mm
[First Sleeve and Second Sleeve]
 Metal slit sleeves
[Laser Light]
 Wavelengths: 405 nm and 635 nm
 Output power: 1 mW to 0.1 mW A table of FIG. 2 shows evaluation results of samples A and B of the first fiber stub 16 and the second fiber stub 18. Note that the lengths of the first GI fiber 24 and the second GI fiber 34 shown in the columns of the samples A and B are actual measured values. Since the lengths of the first fiber stub 16 and the second fiber stub 18 are adjusted by grinding their both ends, they have approximately ±20% of variation in length.

As can be clearly seen from the evaluation results of FIG. 2, the connection loss of the connection structure 10 according to the present invention were as small as from 0.9 dB to 1.4 dB (18% to 28%). It is considered that the difference in the connection loss between the samples A and B was caused by the difference of contact state between the optical fibers and the GI fibers where the PC connection was made. Although the ferrules 15 and 19 and the stubs 16 and 18 were inclined by several degrees at the connection positions of the first sleeve 17, the second sleeve 20 and the connection sleeve 21, the loss hardly increased. Moreover, in the case where the first sleeve 17, the second sleeve 20 and the connection sleeve 21 were replaced with zirconia sleeves, low loss properties were similarly obtained.

Figure 3:
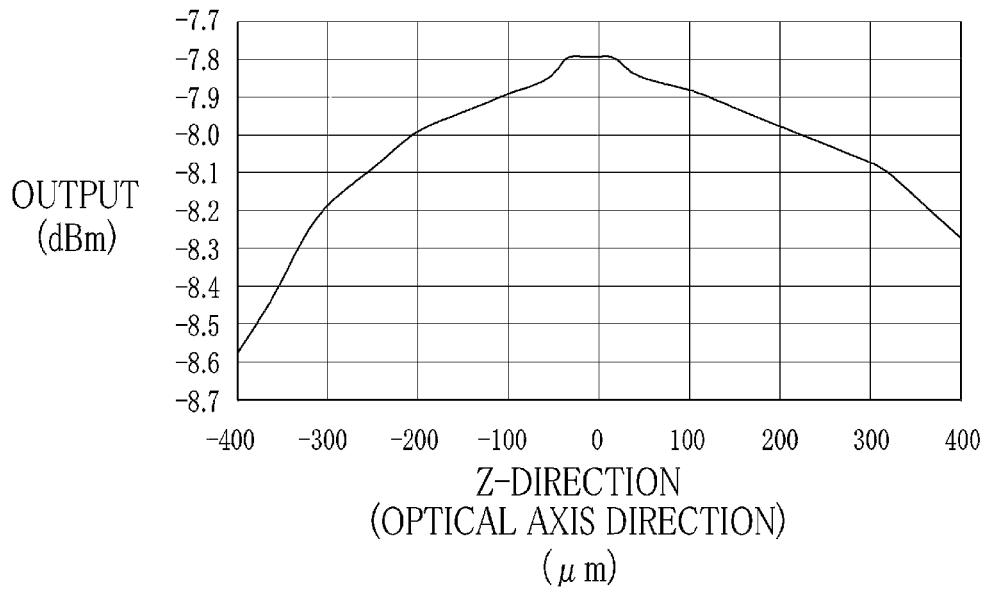
FIG. 3 is a graph showing a tolerance curve in an optical axis direction (Z-direction)
Figure 4:
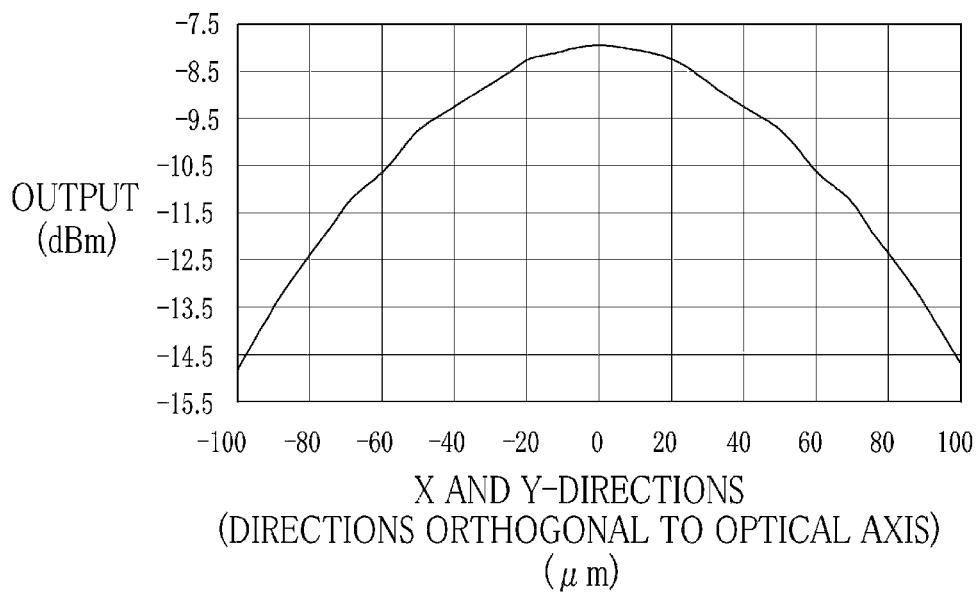
FIG. 4 is a graph showing a tolerance curve in directions orthogonal to the optical axis direction (X and Y-directions)

Graphs of FIGS. 3 and 4 show tolerance curves representing an output of the laser light from the second optical fiber 12 when the relative position between the first fiber stub 16 and the second fiber stub 18 is shifted in the optical axis direction (Z-direction), and X and Y-direction which are orthogonal to the Z-direction. In the Z-direction, a direction in which the first fiber stub 16 and the second fiber stub 18 approach each other is defined as a positive direction. In the X and Y-directions, a shift amount in the Z-direction is zero "0". The above-described tolerance curves are the measurement results on conditions that the lengths of the first fiber stub 16 and the second fiber stub 18 are in the range of 3.5 mm to 5.0 mm, a tolerance in the Z-direction is ±100 μm, and a tolerance in the X and Y-directions is ±20 μm.

As can be seen from the graphs of FIGS. 3 and 4, a decreased amount in the output of the laser light with respect to a shifted amount of the relative position between the first fiber stub 16 and the second fiber stub 18 is relatively small. Accordingly, the connection structure 10 according to the present invention has wide (high) tolerance and maintains low connection loss properties, even if the relative position between the first fiber stub 16 and the second fiber stub 18 is shifted.

The beam diameter (105 μm) of the laser light transmitted by the first optical fiber 11 is expanded approximately five times by using the first GI fiber 24 having the core diameter of 500 μm, like the above-described samples A and B. As a result, the optical power density at the exit surface of the first GI fiber 24 becomes $\frac{1}{25}$ of the optical power density at the tip of the first optical fiber 11. Therefore, if the optical power density at the exit surface of the first GI fiber 24 is set at 15 W/mm$^2$, which is a value enabling prevention of the dust collection, the laser light of 3 W can be transmitted. Accordingly, the connection structure 10 of the present invention is applicable to a high-intensity laser light illumination device.

The core diameters of the GI fibers used for the first fiber stub 16 and the second fiber stub 18 can be at least five times larger than the core diameter of the first optical fiber 11. For example, when the first optical fiber 11 and the second optical fiber 12 are connected by the connection structure using the GI fibers having a core diameter of 1000 μm and a clad diameter of 1250 μm, similar results to the samples A and B were obtained in the case where the first fiber stub 16 and the second fiber stub 18 were approximately 9 mm in length. In the case of using ferrules of a standard size (for example, a diameter ϕ of 2.5 mm or 1.25 mm), the external diameter of the GI fibers is preferably 1000 μm or less.

Figure 5:
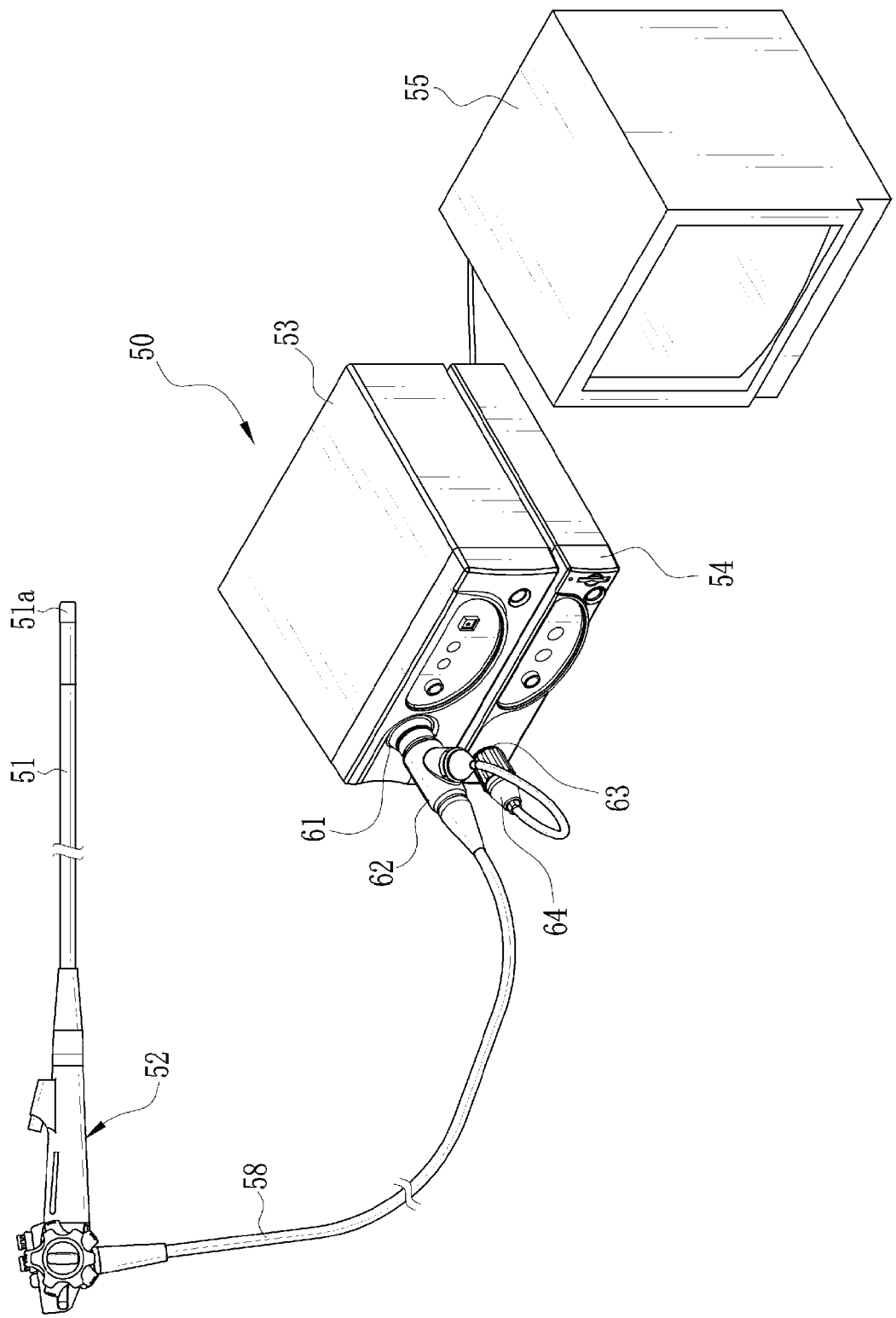
FIG. 5 is a perspective view of an endoscope system using the connection structure of the present invention.

Since the connection structure 10 according to the present invention is suitable for connecting the optical fibers that are frequently attached and detached, the connection structure 10 is applicable to an endoscope system using a laser light illumination device. The endoscope system using the connection structure of the present invention is explained with reference to FIG. 5. The same reference numerals denote the same components as the above embodiment, and detailed description thereof is omitted.

An endoscope system 50 is constituted of an endoscope 52 having an insertion section 51 to be introduced into the body to image the inside of a human body, a light source unit 53 for providing the endoscope 52 with laser light for lighting, a processor unit 54 for processing an image captured by the endoscope 52, and a monitor 55 for displaying the image processed by the processor unit 54.

The endoscope 52 is provided with a universal cord 58, which is connected to the light source unit 53 and the processor unit 54. A communication cable is inserted through the universal cord 58 to send an image signal from an image sensor provided at a distal portion 51a of the insert section 51 to the processor unit 54. The above-described second optical fiber 12 is routed through the insertion section 51 and the universal cord 58. The front end of the second optical fiber 12 is connected to a phosphor in the distal end 51a of the insertion section 51.

An end of the universal cord 58 is provided with a light source connector 62, which is detachably connected to a socket 61 of the light source unit 53. From the light source connector 62, a processor connector 64 is branched to connect the communication cable to the processor unit 54 via a socket 63.

The socket 61 of the light source unit 53 contains the first optical fiber 11, the first ferrule 15, the first fiber tub 16, the first sleeve 17, and the connection sleeve 21, all of which are described above. The first optical fiber 11 is connected to a laser module in the light source unit 53. The light source connector 62 contains the second fiber stub 18, the second ferrule 19, the second optical fiber 12 extending from the universal cord 58, and the second sleeve 20. Thus, the socket 61 and the light source connector 62 compose the connection structure 10 of the present invention. By plugging the light source connector 62 into the socket 61, the connection structure 10 is connected.

The laser light emitted from the laser module in the light source unit 53 is transmitted through the universal cord 58 via the connection structure 10 that is composed of the socket 61 and the light source connector 62. The laser light exits from the front end of the second optical fiber 12 at the distal end 51a of the insertion section 51, and excites the phosphor to generate illumination light. Accordingly, it is possible to obtain the illumination light of high brightness, as compared to a conventional light source unit using a xenon lamp or the like.

The light source connector 62 is plugged into the socket 61 of the light source unit 53 before use of the endoscope 52, and is unplugged after the use. Thus, this connection structure 10 is frequently connected and disconnected. Conventionally, such frequent connections and disconnections cause adhesion of the dust particle to the tip of the optical fiber, the occurrence of the flaw, damage due to adhesion of the optical fibers, and the like. The endoscope system 50 of this embodiment, on the other hand, uses the connection structure 10 according to the present invention between the light source connector 62 and the socket 61, and hence eliminates these problems.

In the above embodiment, the first optical fiber 11 and the second optical fiber 12 have the same core diameter, but the connection structure 10 according to the present invention is applicable to the connection of the optical fibers having different core diameters. In this case, the core diameter of the first GI fiber 24 may be different from that of the second GI fiber 34.

Although the present invention has been fully described by the way of the preferred embodiment thereof with reference to the accompanying drawing, various changes and modifications are possible in the present invention and may be understood to be within the present invention.

What is claimed is:
1. An optical fiber connection structure for connecting a first optical fiber and a second optical fiber each of which is a multi-mode fiber having a core diameter of at least 100 μm, and for transmitting light having an optical power of at least 100 mW from said first optical fiber to said second optical fiber, said optical fiber connection structure comprising:
  a first graded-index fiber having a core diameter at least three times larger than that of said first optical fiber and being detachably attached to one end of said first optical fiber, said first graded-index fiber expanding a beam diameter of said light from said first optical fiber and collimating said light;
  a second graded-index fiber having a core diameter equal to or larger than that of said first graded-index fiber and being detachably attached to one end of said second optical fiber, said first graded-index fiber and said second graded-index fiber being spaced apart from each other with a predetermined gap, said second graded-index fiber converging said beam diameter of said light from said first graded-index fiber and causing said light enter said second optical fiber;
  a first connection member attached to said end of said first optical fiber such that said end of said first optical fiber is exposed from one end surface of said first connection member;
  a first optical component housing said first graded-index fiber such that a light incident surface and a light exit surface of said first graded-index fiber are exposed from both ends of said first optical component;
  a first holding member for holding said first connection member and said first optical component such that said end of said first optical fiber and said light incident surface of said first graded-index fiber are in contact with each other;
  a second connection member attached to said end of said second optical fiber such that said end of said second optical fiber is exposed from one end surface of said second connection member;
  a second optical component housing said second graded-index fiber such that a light incident surface and a light exit surface of said second graded-index fiber are exposed from both ends of said second optical component;

a second holding member for holding said second connection member and said second optical component such that said end of said second optical fiber and said light exit surface of said second graded-index fiber are in contact with each other; and a joining member for joining said first optical component and said second optical component such that said light exit surface of said first graded-index fiber and said light incident surface of said second graded-index fiber are faced across with a predetermined gap;

wherein the length of said first holding member is shorter than the total length of said first connection member and said first optical component, and the length of said second holding member is shorter than the total length of said second connection member and said second optical component.

2. The optical fiber connection structure described in claim 1, wherein said light has at least one wavelength of 405 nm to 635 nm.

3. The optical fiber connection structure described in claim 1, wherein said diameters of said first graded-index fiber and said second graded-index fiber are at least five times larger than that of said first optical fiber.

4. The optical fiber connection structure described in claim 1, wherein length of said first graded-index fiber is longer than length of said second graded-index fiber.

5. The optical fiber connection structure described in claim 4, wherein a total length of said first graded-index fiber and said second graded-index fiber is ½λ or an integral multiple of ½λ.

6. The optical fiber connection structure described in claim 1, wherein lengths of said first graded-index fiber and said second graded-index fiber are at least 3 mm and at most 10 mm.

7. The optical fiber connection structure described in claim 1, wherein a light exit surface of said first graded-index fiber and a light incident surface of said second graded-index fiber are each provided with an anti-reflection layer having fluoride at its outermost surface.

8. The optical fiber connection structure described in claim 7, wherein a light incident surface of said first graded-index fiber and a light exit surface of said second graded-index fiber are each provided with a fluoride layer.

9. The optical fiber connection structure described in claim 1, wherein said first and second connection members are first and second ferrules, and said first and second holding members are first and second sleeves, and said first and second optical components are first and second fiber stubs, and said joining member is a connection sleeve.

10. The optical fiber connection structure described in claim 1, wherein said first holding member has a cylindrical shape and is provided with a first insertion hole whose inner diameter is smaller than external diameters of said first connection member and said first optical component, and wherein said second holding member has a cylindrical shape and is provided with a second insertion hole whose inner diameter is smaller than external diameters of said second connection member and said second optical component.

11. The optical fiber connection structure described in claim 10, wherein said first holding member has a first slit on a peripheral surface thereof along an axial direction thereof, said first slit giving elasticity to said first holding member in a radial direction thereof, and wherein said second holding member has a second slit on a peripheral surface thereof along an axial direction thereof, said second slit giving elasticity to said second holding member in a radial direction thereof.

12. An endoscope system comprising:

an endoscope for capturing images while illuminating inside a human body using an optical fiber inserted through an insertion section of said endoscope;

a light source unit having a light source generating light with an optical power of at least 100 mW, said light source unit sending said light to said optical fiber; and an optical fiber connection structure for connecting said optical fiber of said endoscope and said light source of said light source unit, including:

a first connection member attached to an end of a first optical fiber such that said end of said first optical fiber is exposed from one end surface of said first connection member;

a first optical component housing a first graded-index fiber such that a light incident surface and a light exit surface of said first graded-index fiber are exposed from both ends of said first optical component;

a first holding member for holding said first connection member and said first optical component such that said end of said first optical fiber and said light incident surface of said first graded-index fiber are in contact with each other;

a second connection member attached to an end of a second optical fiber such that said end of said second optical fiber is exposed from one end surface of said second connection member;

a second optical component housing a second graded-index fiber such that a light incident surface and a light exit surface of said second graded-index fiber are exposed from both ends of said second optical component;

a second holding member for holding said second connection member and said second optical component such that said end of said second optical fiber and said light exit surface of said second graded-index fiber are in contact with each other; and a joining member for joining said first optical component and said second optical component such that said light exit surface of said first graded-index fiber and said light incident surface of said second graded-index fiber are faced each other across a predetermined gap;

wherein the length of said first holding member is shorter than the total length of said first connection member and said first optical component, and the length of said second holding member is shorter than the total length of said second connection member and said second optical component.

13. The endoscope system described in claim 12, wherein said first holding member has a cylindrical shape and is provided with a first insertion hole whose inner diameter is smaller than external diameters of said first connection member and said first optical component, and wherein said second holding member has a cylindrical shape and is provided with a second insertion hole whose inner diameter is smaller than external diameters of said second connection member and said second optical component.

14. The endoscope system described in claim 13, wherein said first holding member has a first slit on a peripheral surface thereof along an axial direction thereof, said first slit giving elasticity to said first holding member in a radial direction thereof, and wherein said second holding member has a second slit on a peripheral surface thereof along an axial direction thereof, said second slit giving elasticity to said second holding member in a radial direction thereof.

* * * * *